(12) United States Patent
Klopf et al.

(10) Patent No.: US 11,857,394 B2
(45) Date of Patent: Jan. 2, 2024

(54) THIGH PROSTHETIC COMPONENT

(71) Applicants: Johannes Klopf, Waldbüttelbrunn (DE); Matthias Klopf, Waldbüttelbrunn (DE)

(72) Inventors: Johannes Klopf, Waldbüttelbrunn (DE); Matthias Klopf, Waldbüttelbrunn (DE)

( * ) Notice: Subject to any disclaimer, the term of this patent is extended or adjusted under 35 U.S.C. 154(b) by 375 days.

(21) Appl. No.: 17/058,802

(22) PCT Filed: May 8, 2019

(86) PCT No.: PCT/EP2019/061844
§ 371 (c)(1),
(2) Date: Nov. 25, 2020

(87) PCT Pub. No.: WO2019/228769
PCT Pub. Date: Dec. 5, 2019

(65) Prior Publication Data
US 2021/0212843 A1 Jul. 15, 2021

(30) Foreign Application Priority Data
May 28, 2018 (DE) ...................... 10 2018 112 724.3

(51) Int. Cl.
*A61F 2/64* (2006.01)
*A61F 2/66* (2006.01)
*A61F 2/74* (2006.01)

(52) U.S. Cl.
CPC ................ *A61F 2/64* (2013.01); *A61F 2/642* (2013.01); *A61F 2/6607* (2013.01); *A61F 2/74* (2021.08); *A61F 2002/6614* (2013.01)

(58) Field of Classification Search
CPC .. A61F 2/502; A61F 2/64; A61F 2/604; A61F 2/642; A61F 2/646; A61F 2/6607; A61F 2/74; A61F 2002/6614; A61F 3/00
See application file for complete search history.

(56) References Cited

U.S. PATENT DOCUMENTS

| 2,568,051 A | 9/1951 | Catranis |
|---|---|---|
| 9,289,317 B2 | 3/2016 | Goldfarb |

(Continued)

FOREIGN PATENT DOCUMENTS

| DE | 39 07 195 A1 | 9/1989 |
|---|---|---|
| DE | 10 2012 023 023 A1 | 5/2014 |

(Continued)

OTHER PUBLICATIONS

Translation of Reignier (FR923517A) (Year: 1947).*
International Search Report in International Patent Application No. PCT/EP2019/061844, dated Sep. 23, 2019 (3 pages).

*Primary Examiner* — Christie Bahena
(74) *Attorney, Agent, or Firm* — ICE MILLER LLP

(57) ABSTRACT

A thigh prosthetic component for connecting to a thigh shaft. The component includes a pivotable knee joint and an upper part and a lower part connected by ventral and dorsal arms. The ventral arm is articulated to the upper part and to the lower part via distinct axes. The dorsal arm is articulated to the upper part and to the lower part via distinct axes. The component further includes an ankle pivotably connecting a foot part to a lower leg unit connected to the knee joint. The lower leg unit has ventral and dorsal connecting elements transmitting thrust and traction. The ventral connecting element is pivoted to the foot part and to the lower part. The dorsal connecting element is articulated to the foot part and to the upper part and the dorsal articulated arm such that an adjustment of the knee joint from stance to swing positions causes a dorsal extension of the foot part.

16 Claims, 16 Drawing Sheets

(56) References Cited

U.S. PATENT DOCUMENTS

| | | |
|---|---|---|
| 9,750,620 B2 | 9/2017 | Goldfarb |
| 2009/0265018 A1 | 10/2009 | Goldfarb et al. |
| 2013/0268092 A1* | 10/2013 | Karlsson ................ A61F 2/68 623/43 |
| 2015/0305895 A1 | 10/2015 | Boiten et al. |

FOREIGN PATENT DOCUMENTS

| | | | | |
|---|---|---|---|---|
| EP | 0095872 A1 | * | 7/1983 | ............... A61F 2/64 |
| EP | 1 447 062 A2 | | 8/2004 | |
| FR | 503538 A | * | 12/1920 | ........... A61F 2/6607 |
| FR | 923517 A | * | 9/1947 | ............. A61F 2/604 |
| FR | 2 549 719 A1 | | 2/1985 | |
| GB | 173124 A | * | 12/1921 | |
| WO | WO-2012119017 A1 | * | 9/2012 | ............... A61F 2/76 |
| WO | WO 2012/131565 A1 | | 10/2012 | |
| WO | WO-2013152281 A1 | * | 10/2013 | ............... A61F 2/64 |
| WO | WO-2016005491 A1 | * | 1/2016 | ............... A61F 2/64 |

* cited by examiner

THIGH PROSTHETIC COMPONENT

CROSS-REFERENCE TO RELATED APPLICATIONS

This application is a U.S. National Stage of International Application No. PCT/EP2019/061844, filed May 8, 2019, which claims the benefit of Germany Patent Application No. 10 2018 112 724.3, filed May 28, 2018, both of which are incorporated herein by reference in their entireties.

The invention relates to a thigh prosthetic component for connecting to a thigh shaft, having:
- a knee joint that can be pivoted between a stance position and a swing position and has a proximal knee joint upper part and a distal knee joint lower part which are connected by a ventral articulated arm and a dorsal articulated arm, wherein
  the ventral articulated arm is articulated to the proximal knee joint upper part via a ventral, upper knee joint axis, and is articulated to the distal knee joint lower part via a ventral lower knee joint axis, and the dorsal articulated arm is articulated to the proximal knee joint upper part via a dorsal, upper knee joint axis, and is articulated to the distal knee joint lower part via a dorsal lower knee joint axis, and
- an ankle for the pivotable connection of a foot part to a lower leg unit connected to the knee joint.

Thigh prostheses with a thigh prosthesis component of the aforementioned type and a thigh shaft are used for the prosthetic treating of a patient, and in so doing replace a nonexistent lower leg including the human knee joint. In addition to the prosthetic knee joint, thigh prostheses have a prosthetic foot that is connected to the prosthetic knee joint by a lower leg unit. The prosthetic knee joint is moreover formed on a thigh stump for attaching the prosthesis, wherein normally thigh shafts are used for this that are connected to the thigh prosthetic component in the region of the knee joint into which the thigh stump can be inserted.

While the thigh prosthesis is being used by the patient, it passes through several movement segments of a gait phase which is also termed a walking cycle, and includes a stance phase and a swing phase. In this case, the stance phase describes the range in which contact with the ground exists via the thigh prosthesis, wherein there is no ground contact during the swing phase. During the stance phase that begins with heel contact by the thigh prosthesis and ends with toe-off, the patient can be supported on the ground by the thigh prosthesis. The stance phase is followed by the swing phase during which the thigh prosthesis is swung from toe-off until heel contact.

A problem for patients with thigh prostheses is in particular that the patient must assume a stronger equinus position during the swing phase while walking with the healthy foot in order for the prosthetic foot of the thigh prosthesis to swing forward with the thigh prosthesis while taking another step. It is in particular therefore necessary to assume a more pronounced equinus position with the healthy foot to prevent the thigh prosthesis from being inhibited by contact with the ground while swinging through during the swinging phase. This compensatory movement while walking is absolutely necessary in order to enable swinging through, and in order to counteract a perceived lengthening of the leg from the prosthesis at the beginning of the swinging phase. Since a perceived shortening of the leg that is necessary for swinging through only begins at a knee flexion of 30° to 50° depending on the knee joint type, a high exertion of energy is needed by the patient to achieve the required ground clearance and prevent stumbling. Since the patient cannot sustain this exertion over the long term, a compensatory movement occurs with a contralateral equinus position and a circumduction of the prosthetic side. Alternatively, the prosthesis can be designed shorter which produces a limp. Another disadvantage of the movement process required for swinging forward is its unphysiological manner of movement that results in a greater load on the remaining parts of the body, in particular the spinal column.

Against this backdrop, the object of the invention is to provide a thigh prosthetic component that enables a natural gait pattern and is more energy-efficient and stable for the patient.

The invention achieves the object with a thigh prosthetic component having the characteristics of claim 1. Advantageous further embodiments of the invention are set forth in the dependent claims. Within the context of the following explanation of the invention, it is assumed that a thigh prosthesis has a loaded thigh component and a nonloaded thigh shaft connected to the thigh component.

The knee joint of the thigh prosthetic component according to the invention is configured by the use of a proximal knee joint upper part and a distal knee joint lower part and their connection by a ventral and a dorsal articulated arm as a polycentric swivel joint. Consequently, the pivot point of the knee joint results from the intersection of the longitudinal axes of the articulated arms that, with respect to the ventral articulated arm, extend through the ventral upper and ventral lower knee joint axis and, with respect to the dorsal articulated arm, extend through the dorsal upper and dorsal lower knee joint axis. The advantage of such a polycentric knee joint is that this allows the effective pivot point of the knee joint to be adapted by the design so that it is loaded during the gait phase in the segment between heel contact up to just before toe-off, i.e., while the thigh prosthesis is being loaded by the patient while walking and the knee joint is in an extension stop, behind which the load line is positioned when using the thigh prosthesis. Only when tow-off is actually reached, i.e., at the end of the loading phase of the thigh prosthesis and with the beginning of the swing phase in which the thigh prosthesis is swinging forward unloaded below the body, is it possible for the load line to run in front of the pivot point of the knee joint which causes the knee joint to flex, and the swing-through phase can follow until renewed heel contact. The pivot point can also be aligned in that the pivot point runs behind the load line during the entire stance phase, the knee joint is located in an extension stop, and then the swing phase must be actively initiated by the patient against a certain resistance that depends on the position of the pivot point relative to the load line.

The embodiment according to the invention provides that the lower leg unit has both a ventral as well as a dorsal connecting element which can transmit thrust as well as traction. The ventral and the dorsal connecting element are articulated by a ventral, or respectively dorsal ankle axis to the foot part. At its ends opposite the foot part, the ventral connecting element is articulated to the distal knee joint lower part, and the dorsal connecting element is articulated via the dorsal upper knee joint axis to the proximal knee joint upper part as well as the dorsal articulated arm.

The connection via the lower leg unit is such that when the knee joint flexes in the toe-off, i.e., at the end of the loading phase and at the beginning of the swing phase, there is a dorsal extension of the foot part. In so doing, there is a pivoting of the foot part that can be connected to conventional prosthetic feet about the dorsal and ventral ankle axis that run parallel to each other. The lifting of the toe region into the swing position occurring during dorsal extension, i.e., at the beginning of the swing-through phase of the thigh prosthesis, causes an increase in the distance between the foot part of the thigh prosthesis and the ground and accordingly makes it possible to avoid a formation of the equinus position. Moreover, the dorsal extension brought about by the flexing of the knee promotes an energy-saving initiation of the swing phase. The thigh prosthetic component according to the invention therefore enables a more natural gait in comparison to conventional thigh prostheses, wherein walking safety is also simultaneously enhanced by the generated dorsal extension since potential stumbling due to an insufficient distance from the ground by the foot part when swinging through is effectively prevented.

As already described above, the intersection of the longitudinal axes of the ventral and dorsal articulated arm determine the pivot point of the knee joint of the thigh prosthetic component. According to a further embodiment of the invention, it is provided that an adjusting unit is provided which is designed to align the ventral articulated arm relative to the dorsal articulated arm in the stance position of the knee joint, i.e., in its unflexed position.

In use, i.e., during the gait phase, the thigh prosthesis is in the stance position from the beginning of loading starting with heel contact up to toe-off in which the knee joint is in an extension stop and is not flexed. Depending on the position of the pivot point, the load line shifts just before toe-off to behind the pivot point defined by the ventral and dorsal articulated arm which transfers the knee joint into the swing position by means of flexion. If the pivot point does not shift to behind the load line before toe-off, the swing phase must be actively initiated by the patient against a resistance. A further development of the invention provides that the ventral articulated arm can be aligned relative to the dorsal articulated arm by an adjusting unit. The possibility of an orientation of the dorsal and ventral articulated arm relative to each other, i.e., changing the angle position of these two articulated arms relative to each other, makes it possible to shift the intersection of the longitudinal axes of the two articulated arms, and hence the pivot point of the knee joint. The adjusting unit therefore offers the option of adapting the thigh prosthesis to patient-specific requirements in order to therefore enable a natural gait. The pivot point is aligned taking into account the set requirements such as flexion shortly before toe-off, as well as a simultaneously stable arrangement of the knee joint in the stance position at the end of the swing phase and with the beginning of the stance phase that starts with heel contact by the foot part after the thigh prosthesis swings through. Alternatively, the pivot point can also be aligned by the adjusting unit, for example, so that flexion must be actively brought about at the end of the stance phase, wherein the resistance to be overcome for this can be adjusted by the adjusting unit.

The adjusting unit can in principle be designed in any desired way to the extent that it can reliably achieve an establishment of the orientation of the two articulated arms in the stance position. According to a particularly advantageous embodiment of the invention, it is provided however that the adjusting unit has an adjusting element, in particular a set screw, that is adjustably mounted on the dorsal articulated arm and rests against a stop surface of the dorsal connecting element in the stance position.

According to this embodiment of the invention, the dorsal articulated arm adjoins a stop surface of the dorsal connecting element when the knee joint is in the stance position and thereby establishes the position of the knee joint in the stance position. Using an adjustable adjusting element arranged on the dorsal articulated arm, in particular a set screw that projects from the dorsal articulated arm toward the dorsal connecting element during use and lies against the stop surface in the stance position, easily makes it possible to change the distance between the stop surface and the dorsal articulated arm in the region of the adjusting element, in particular the set screw which changes the location of the dorsal articulated arm relative to the ventral articulated arm.

This embodiment of the invention is characterized in that it allows the pivot point of the knee joint to be established in a particularly easy and reliable manner. In particular, the use of a set screw is distinguished in that it enables a very precise, smooth and reliable establishment of this pivot point, and can simultaneously be designed very easily and economically. Very advantageously, the stop surface has a recess adapted to the end of the adjusting element, in particular the set screw, in the region of the adjusting element, in particular the set screw, which reliably prevents the screw from escaping and enhances the reliability of positioning the dorsal articulated arm relative to the ventral articulated arm in a complementary manner. In the case of using a set screw, its threaded joint is preferably designed to be self-locking so that the set position is reliably secured.

Given a flexion angle of up to 90°, the patient is also able to assume a seated position by flexing the knee joint, wherein the knee joint subsequent to toe-off during the swing phase is arranged in the swing position in which the knee joint however has a slighter flexion angle. According to an advantageous embodiment of the invention, setting the maximum possible flexion, i.e., establishing a maximum flexion angle, is however provided, wherein the knee joint upper part and the knee joint lower part are preferably operatively connected so that a maximum flexion of the knee joint can be adjusted. This can in principle be done in any desired manner, wherein a mechanical limit to the maximum flexion, for example by suitable stop means, is preferably provided. According to a particularly advantageous embodiment of the invention, it is provided however that the dorsal articulated arm has a flexion stop lying against the proximal knee joint upper part in the swing position.

According to this embodiment of the invention, the dorsal articulated arm has a stop body that is designed and arranged on the dorsal articulated arm such that pivoting of the dorsal articulated arm from the stance position in the direction of the swing position is limited, wherein a stop element arranged on the dorsal articulated arm is brought into contact with the proximal knee joint upper part. This embodiment of the invention is distinguished by its particular simplicity and compactness and makes it possible to limit in a reliable manner the maximum pivotability of the dorsal articulated arm in the direction of the swing position. The limitation provides an effective protection against stumbling with a simultaneously sufficient dorsal extension during the swing phase. The thigh prosthesis further developed in this manner prevents greater pivoting, i.e., due to the flexion stop, so that the patient, in stumbling, can be reliably supported by the then stable knee joint arranged in the swing position and can prevent a fall. The knee flexion that exists during stumbling in conjunction with a dorsal extension of the foot moreover also ensures full ground contact with the foot during stumbling, which makes it possible for the patient to accommodate the stumbling as an almost normal step, wherein the load line has a normal path and extends through the foot and hip. This effectively prevents a fall as a consequence of stumbling.

In principle, the embodiment of the preferred provided flexion stop is freely selectable. In its simplest embodiment, it can accordingly be designed as a stop element projecting from the dorsal articulated arm that, in the swing position, lies against the proximal knee joint upper part which prevents greater flexion. Such a stop element can be arranged in this case in consideration of a sufficient dorsal extension and therefore a sufficient ground clearance while swinging through, and in consideration of simultaneously sufficient support in the event of possible stumbling. According to an advantageous further development of the invention, it is provided however that the flexion stop is adjustably arranged on the proximal knee joint upper part to establish the swing position.

The adjustable arrangement of the flexion stop makes it possible to comfortably adjust the maximum possible flexion angle in consideration of the patient-specific conditions. This enhances, in a complementary way, the individual adaptability of a thigh prosthesis further developed in this manner.

According to another embodiment of the invention, it is furthermore provided that the ventral connecting element and/or the dorsal connecting element are designed changeable in length. Given an embodiment of one or both connecting elements that is changeable in length, it is possible to adapt the thigh prosthesis in a comfortable way to the patient-specific requirements, in particular the needed length. Separate adjustability of the dorsal and ventral connecting element makes it possible in this case to respond to individual particularities of the patient in a very easy manner.

The design of the ventral connecting element as well as the dorsal connecting element is in principle freely selectable in this case. According to an advantageous embodiment of the invention, it is provided however that the ventral connecting element has a ventral foot element articulated to the foot part, and a ventral lower leg rod. The lower leg rod in this case is connected to the ventral foot element and/or to the distal knee joint lower part in a manner that can be adjusted in the direction of its longitudinal axis. Given a possibility of adjusting the lower leg rod in the direction of its longitudinal axis with the distal knee joint lower part and/or the ventral foot element, it is possible to adapt the longitudinal extension of the ventral connecting element and therefore the entire thigh prosthesis in a very easy manner. In this case, a possible adjustability in the direction of the longitudinal axis can be realized in a very easy manner by the ventral lower leg rod having threaded sections on the end that enable a precise axial adjustment and fixation of the lower leg rod. In so doing, securing the adjusted position can be achieved for example by suitable locking elements such as lock nuts.

Analogous to the above-described advantageous further embodiment of the ventral connecting element, another embodiment of the invention provides that the dorsal connecting element has a dorsal foot element articulated to the foot part and a dorsal lower leg rod, wherein the lower leg rod is connected to the dorsal foot element and/or to the proximal knee joint upper part in a manner that can be adjusted in the direction of its longitudinal axis.

The advantageously provided longitudinal adjustability of the dorsal lower leg rod makes it possible, in particular in conjunction with the advantageously provided adjustability of the ventral connecting element, to precisely adapt the thigh prosthesis to patient-specific needs. The option of adjustability allows anatomical conditions to be addressed and to provide a thigh prosthesis optimally adapted to the patient.

The knee joint upper part serves to connect the thigh prosthetic component to a thigh stump of the patient, and it is provided with a shaft seat for connecting to a thigh shaft in which the thigh stump can be inserted. According to a further development of the invention, it is provided that the proximal knee joint upper part has a support and a shaft seat articulated to the support that can be adjusted between a walking and seated position.

With this embodiment of the invention, the proximal knee joint upper part of the thigh prosthetic component also has a monocentric joint in addition to the knee joint with a polycentric design that is formed by the articulated connection of the support to the shaft seat. The pivotability of the shaft seat arranged proximally to the knee joint relative to the support makes it possible for the user, if needed, to also flex the knee beyond the flexion stop provided according to one advantageous development of the invention. Further flexing facilitates sitting or climbing stairs. The pivotability of the support relative to the shaft seat can also be limited in this case, for example by suitable stop means on the support, and/or on the shaft seat, and/or by being designed dampened, or respectively cushioned, for example by using a hydraulic cylinder that is arranged between the support and the shaft seat.

According to another embodiment of the invention, it is provided that, given the advantageous design of the proximal knee joint upper part with a support and an articulated shaft seat, the support is articulated by the dorsal upper knee joint axis to the dorsal articulated arm and the dorsal connecting element, and is articulated by the ventral, upper knee joint axis to the shaft seat. This embodiment of the invention enables a very simple and compact design of the thigh prosthesis and enables the thigh prosthesis to be precisely adapted to the needs of the patient, also given an advantageously provided design of the proximal knee joint upper part with the support and shaft seat being articulated to each other.

In principle, the constructive design of the articulated connection of the shaft seat to the support is freely selectable. This also comprises the construction of the articulated connection such that it is only adjusted from the walking to seated position in case of need, and moreover it is ensured that the shaft seat is in the walking position and has sufficient stability to ensure reliable support for the user during the gait phase.

According to an advantageous embodiment of the invention, it is provided that the shaft seat is unlockably locked on the support in walking position. Locking the shaft seat on the support ensures more particularly that the thigh prosthesis can be reliably flexed solely via the knee joint during the normal gait phase. Accidentally adjusting the further developed proximal knee joint upper part from the walking to the seated position is effectively prevented by a lock. In case of need, it is possible to undo the lock by unlocking so that an adjustment of the proximal knee joint upper part from the walking to the seated position can then be performed in a comfortable manner.

Alternatively or in addition, the shaft seat can also be positioned in the walking position by a sufficiently dimensioned spring element such as a gas pressure spring or a hydraulic spring so that for example sitting, or ascending, or descending against a flexural resistance of the spring element can occur.

According to another embodiment, it is furthermore provided that the shaft seat is pretensioned on the support in the direction of the walking position such that the pretension is blocked in seated position. Pre-tensioning the shaft seat relative to the support in the direction of the walking position ensures more particularly that the support of the shaft seat is located in the walking position during normal operation. Such pretensioning can ensure a reliable arrangement of the shaft seat in the walking position independently or in addition to the advantageously provided locking of the shaft seat in the walking position.

According to this further embodiment of the invention, it is provided however that the pretensioning does not have a resetting effect in the seated position after flexing the knee by pivoting the support and shaft seat approximately 90°. Annulling the effect of pretensioning in the region of the seated position prevents the thigh prosthesis from independently assuming the walking position in a seated state because of unblocked pretension. Such a blocking pretension can for example be achieved by a suitable arrangement of the attachment points of a spring element on the shaft seat and for example distal knee joint lower part that causes the spring element in the region of the seated position to be located in a top dead center position so that the pretension even causes the seated position to be secured in position.

In principle, the shaft seat can be locked on the support in any desired way in the walking position. According to another embodiment of the invention, it is however provided that a locking body that can be adjusted between a locked position and an unlocked position is arranged on the shaft seat and can be brought into engagement with a latching recess in the support in the locked position.

This design of interlocking is a particularly simple and economical solution for locking the shaft seat in the walking position. The locking body can be moved out of the latching recess by a simple manual adjustment, and thereby enables the user to adjust the shaft seat out of the walking position into the seated position. The shaft seat is then relocked in the walking position by a return movement of the locking body, wherein according to a particularly advantageous embodiment, the locking body is pretensioned in the direction of the locked position. This secures the walking position in a special way, and ensures independent locking by a return movement.

Exemplary embodiments of the invention will be described below with reference to the drawings. In the drawings.

Figure 1:
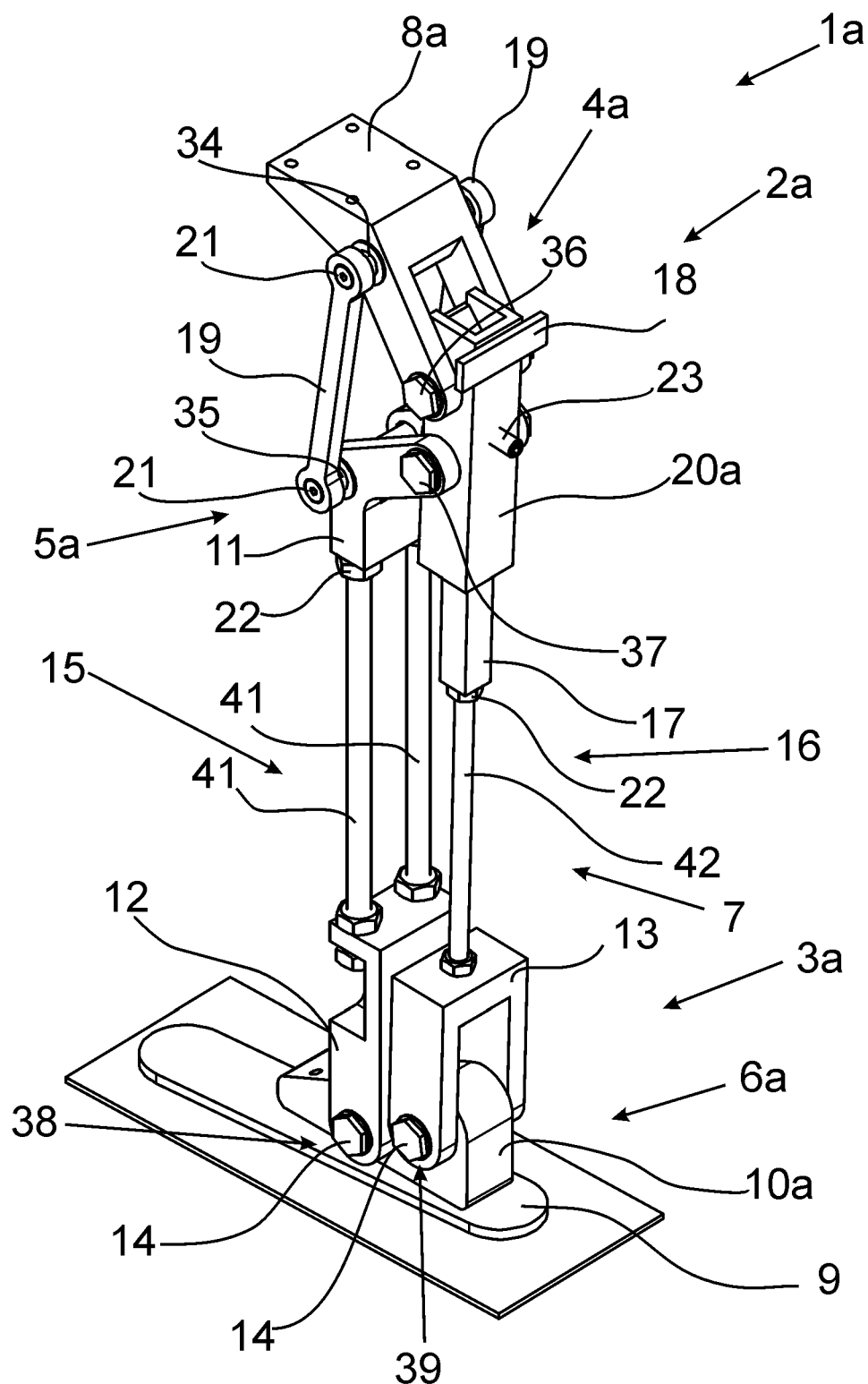
FIG. 1 shows a perspective view of a first embodiment of a thigh prosthesis in a stance position.

A thigh prosthetic component $1a$ shown in a perspective view in FIG. 1 has a knee joint $2a$, a foot part unit $6a$ with an ankle $3a$ as well as a lower leg unit 7 as essential assemblies.

The knee joint $2a$ possesses a proximal knee joint upper part $4a$ that is articulated to a distal knee joint lower part $5a$. The proximal knee joint upper part $4a$ has a shaft seat $8a$ by means of which the thigh prosthetic component $1a$ is connected to the patient by, for example, a thigh shaft which is not shown in this case. The shaft seat $8a$ is designed as a single part and is connected by a ventral upper knee joint axis 34 to two ventral articulated arms 19 arranged on opposite sides of the shaft seat $8a$. The articulated arms 19 are secured to the shaft seat $8a$ by countersunk screws 21. Moreover, the shaft seat $8a$ designed as a single part is articulated by a dorsal upper knee joint axis 36 to a dorsal articulated arm $20a$ with a U-shaped cross-section, wherein the position of the shaft seat $8a$ on the dorsal articulated arm $20a$ is secured by flathead screws 14.

At their ends opposite the shaft seat $8a$, the articulated arms 19 are also articulated by a ventral lower joint axis 35 formed by a shaft 24 to a knee lower part 11 of the distal knee joint lower part $5a$, wherein the ends of the articulated arms 19 opposite the shaft seat $8a$ are also secured in their position by countersunk screws 21. The knee lower part 11 is moreover also connected by a dorsal lower knee joint axis 37 to the dorsal articulated arm $20a$. The knee joint $2a$ designed in this manner is accordingly a polycentric joint whose pivot point results from the intersection of the straight lines running a direction of longitudinal axis through the ventral articulated arms 19 and the dorsal articulated arm $20a$.

The knee joint $2a$ designed in the above-mentioned manner is connected at its distal end by a ventral connecting element 15 as well as a dorsal connecting element 16 to a foot part $10a$. The dorsal connecting element 16 has a dorsal lower leg rod 42 that is connected at one end to a coupling element 17 which is connected at its end opposite the dorsal lower leg rod 42 by the dorsal upper knee joint axis 36 to the shaft seat $8a$. The dorsal lower leg rod 42 can be screwed into the coupling element 17 for adjustment in the direction of longitudinal axis, wherein the set position is secured relative to the coupling element 17 by a hexagon nut 22.

At its end opposite the coupling element 17, the dorsal lower leg rod 42 is screwed into a dorsal foot element 13, wherein the effective longitudinal extension of the dorsal lower leg rod 42 can be set by the screw-in length. The position of the dorsal lower leg rod 42 is secured on the dorsal foot element 13 by a hexagon nut 22. For its part, the dorsal foot element 13 is articulated by a dorsal ankle axis 39 to the foot part $10a$ and is secured with flathead screws 14.

The knee lower part 11 is furthermore connected to a ventral foot element 12 by two ventral lower leg rods 41 of the ventral connecting element 15 that extend parallel to each other, wherein the effective longitudinal extension of the ventral lower leg rods 41 can be fixed between the knee lower part 11 and the ventral foot element 12 because the ventral lower leg rods 41 can be screwed into the knee lower part 11 and the ventral foot element 12. The set position of the ventral lower leg rods 41 on the knee lower part 11 and the ventral foot element 12 is secured by hexagon nuts 22. Like the dorsal foot element 13, the ventral foot element 12 is also articulated by a ventral ankle axis 38 to the foot part 10a, wherein the position of the ventral foot element 12 on the foot part 10a is secured by flathead screws 14. A foot plate 9 is rigidly fastened to the foot part 10a by which ground contact is established.

To establish the pivot point of the knee joint 2a that results from the intersection of the straight lines which extend through the ventral upper knee joint axis 34 and the ventral lower knee joint axis 35 on the one hand and the dorsal upper knee joint axis 36 and the dorsal lower knee joint axis 37 on the other hand, an adjusting element designed as a set screw 23 is arranged on the dorsal articulated arm 20a. In this case, the set screw 23 is arranged within a threaded through-hole in the articulated arm 20a and, depending on the screw-in depth, extends by its ventral end toward a contact surface 33 of the coupling element 17. Depending on the screw-in depth, the longitudinal orientation of the articulated arm 20a is aligned and, moreover the longitudinal orientation of the articulated arms 19 is adjusted via the connection of the articulated arm 20a to the knee lower part 11, which altogether can shift the intersection of these straight lines defining the pivot point of the knee joint 2a.

Figure 2:
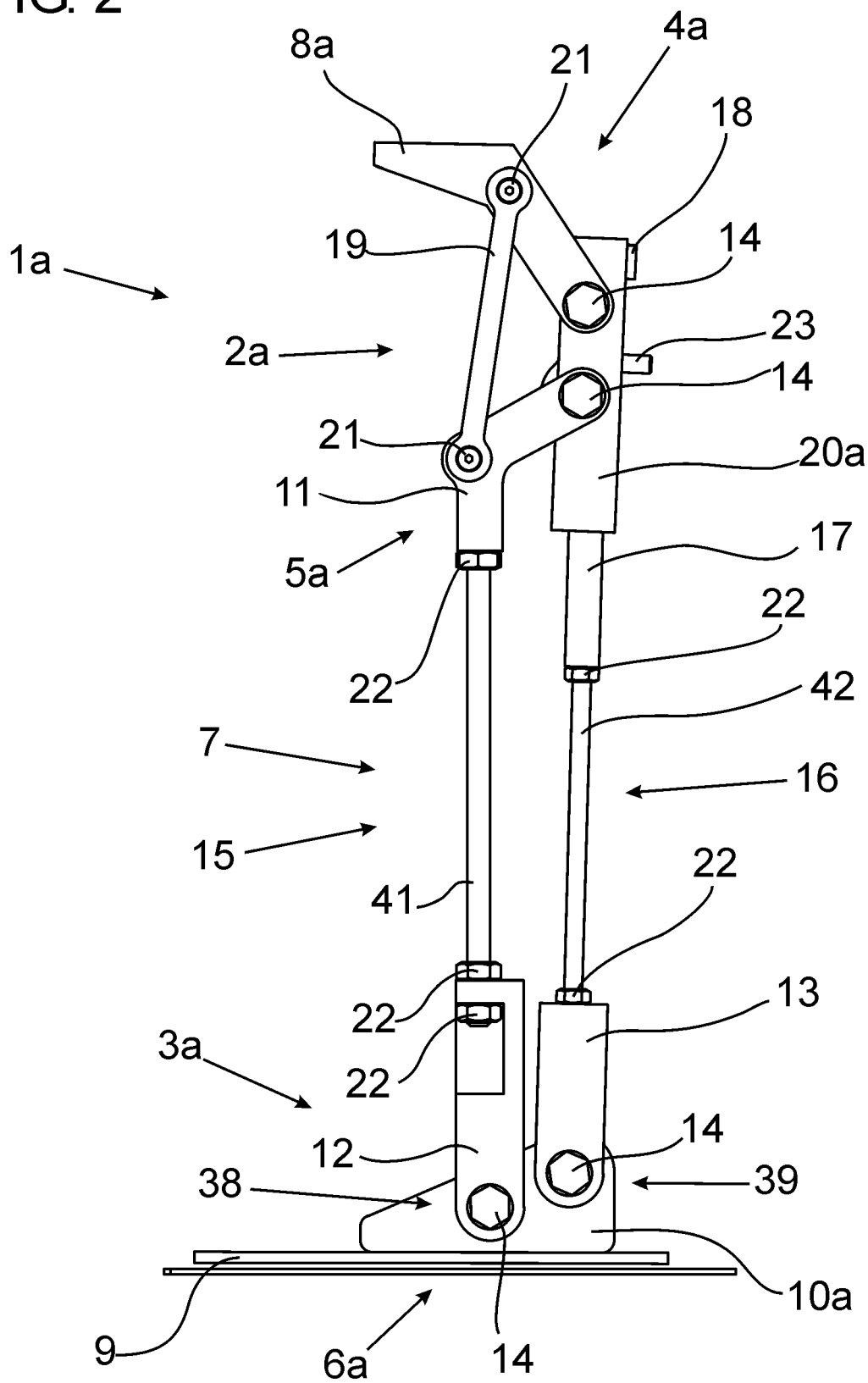
FIG. 2 shows a side view of the thigh prosthesis from FIG. 1 in the stance position.
Figure 3:
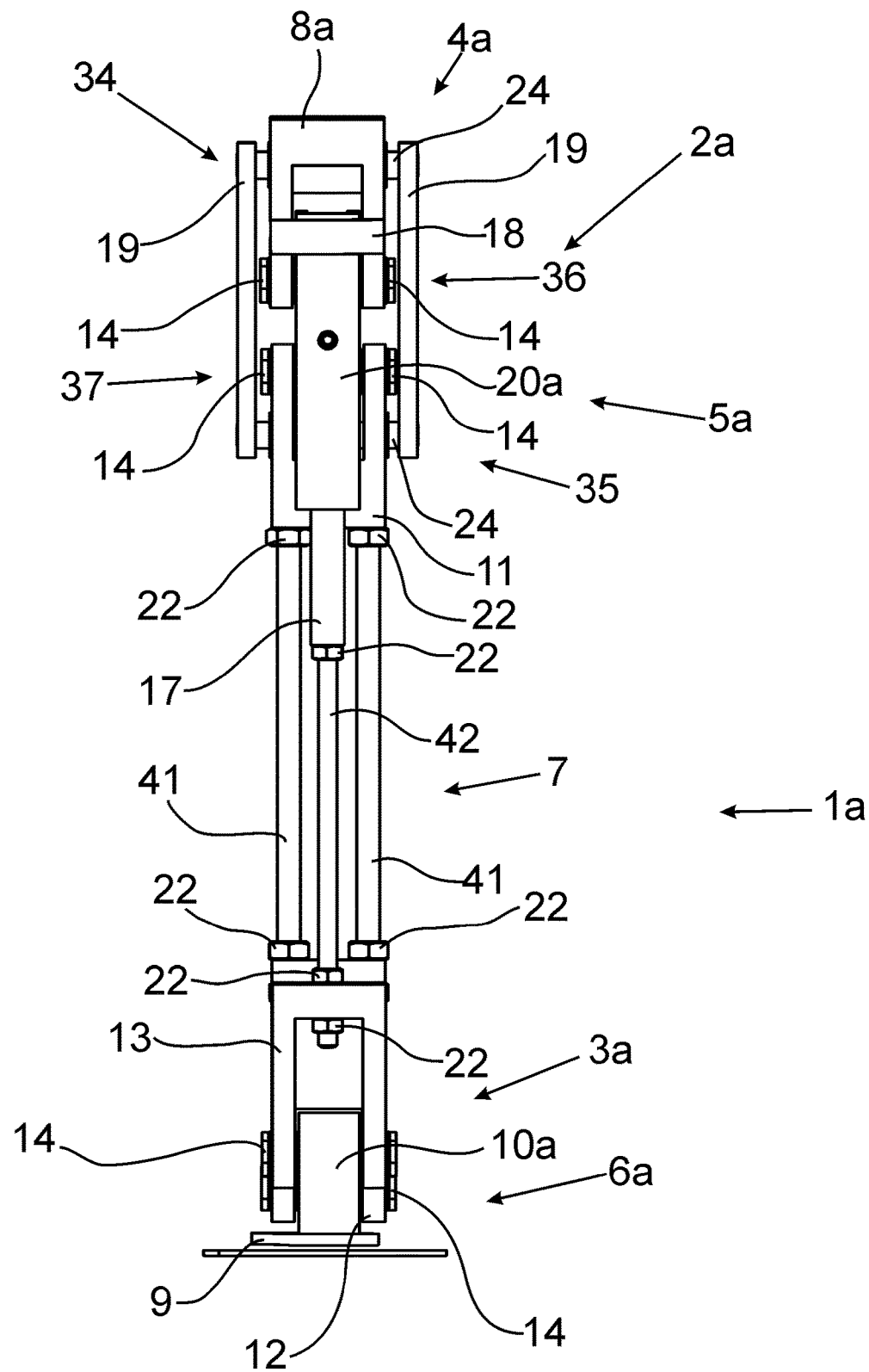
FIG. 3 shows a rear view of the thigh prosthesis from FIG. 1 in the stance position.
Figure 4:
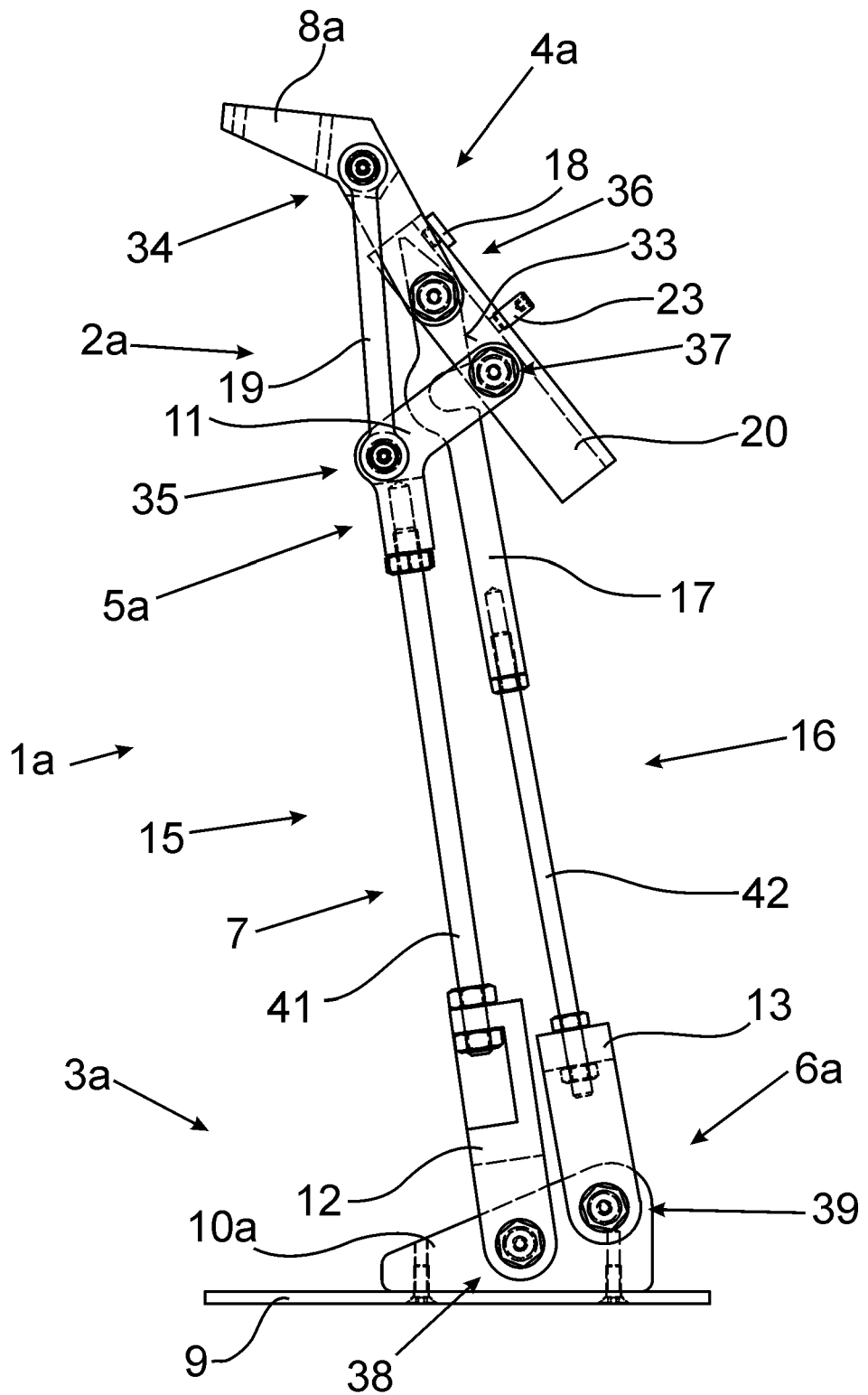
FIG. 4 shows a side view of the thigh prosthesis from FIG. 1 with a flexed knee joint arranged in a swing position.
Figure 5:
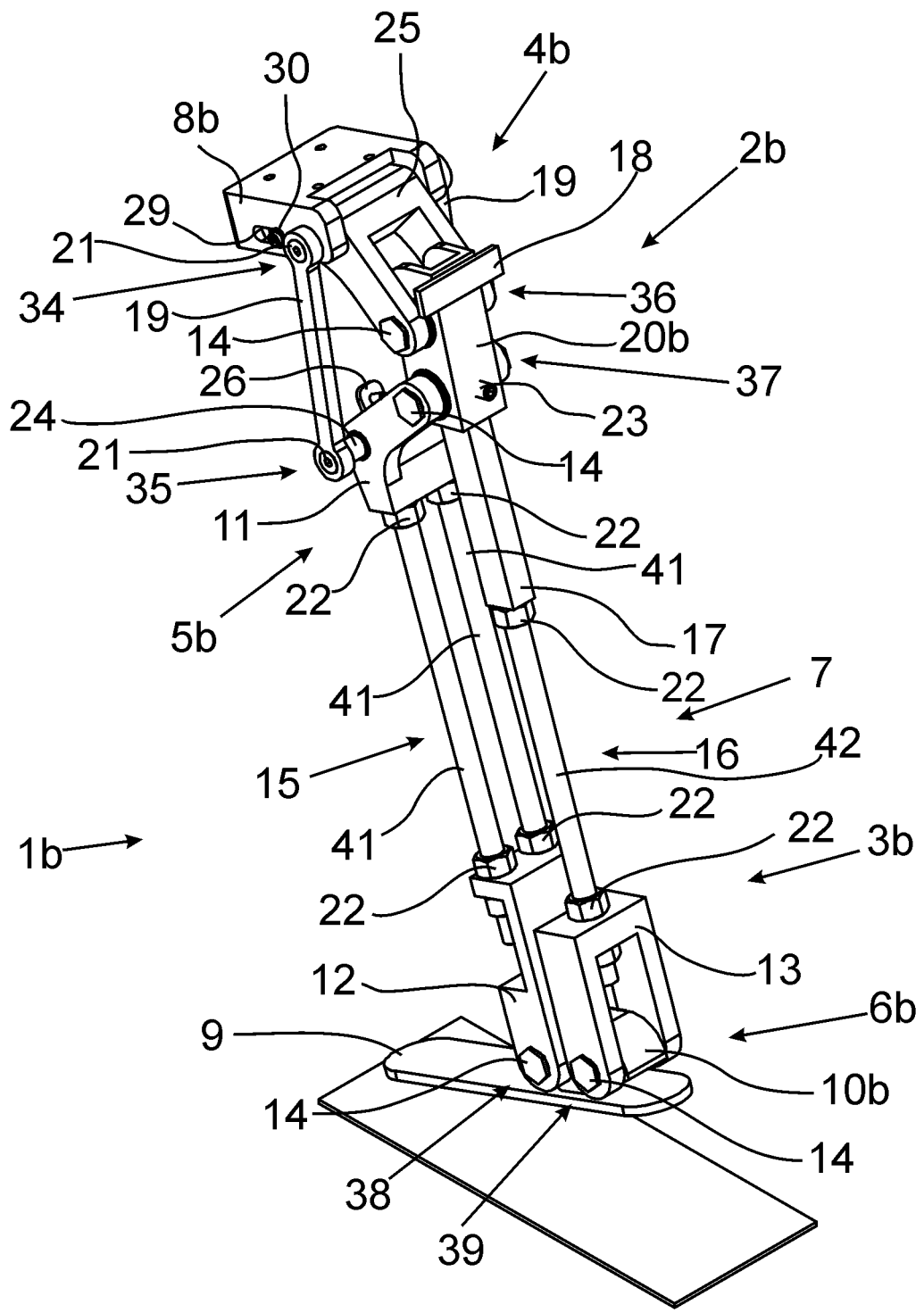
FIG. 5 shows a perspective view of a second embodiment of a thigh prosthesis at the end of a stance phase.
Figure 6:
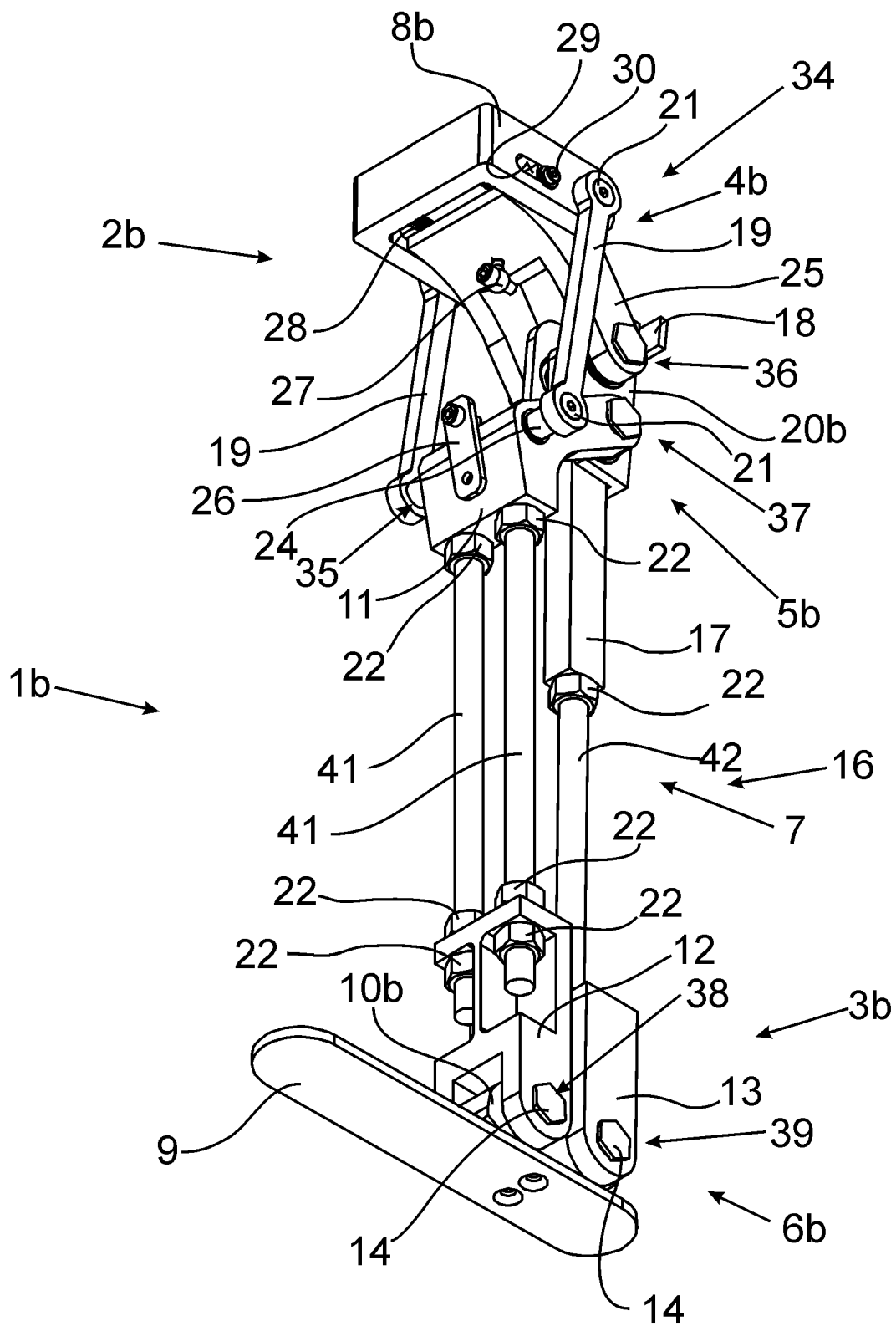
FIG. 6 shows another perspective view of the thigh prosthesis from FIG. 5 in the stance position of the knee joint.
Figure 7:
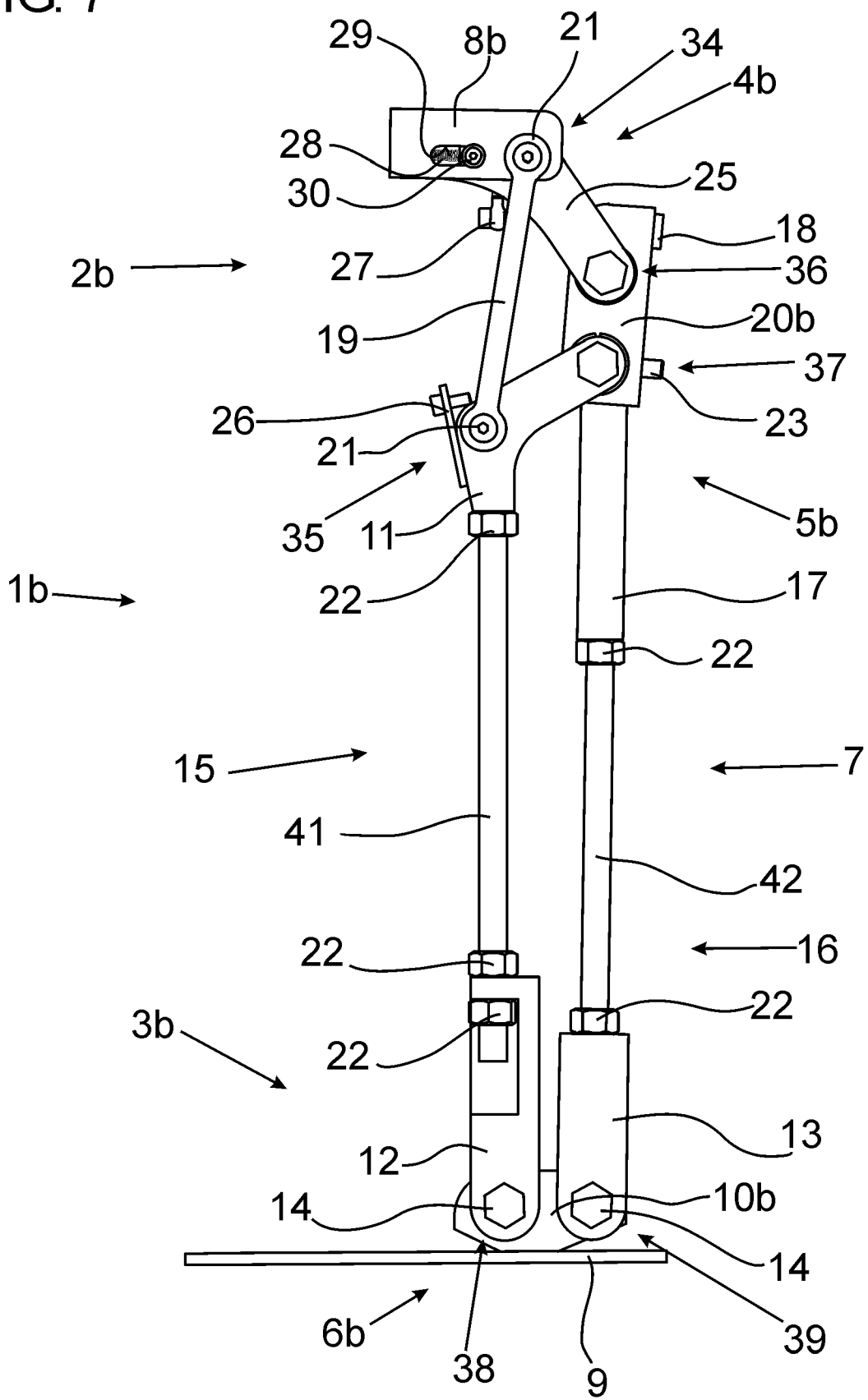
FIG. 7 shows a side view of the thigh prosthesis from FIG. 5 in the stance position of the knee joint.
Figure 8:
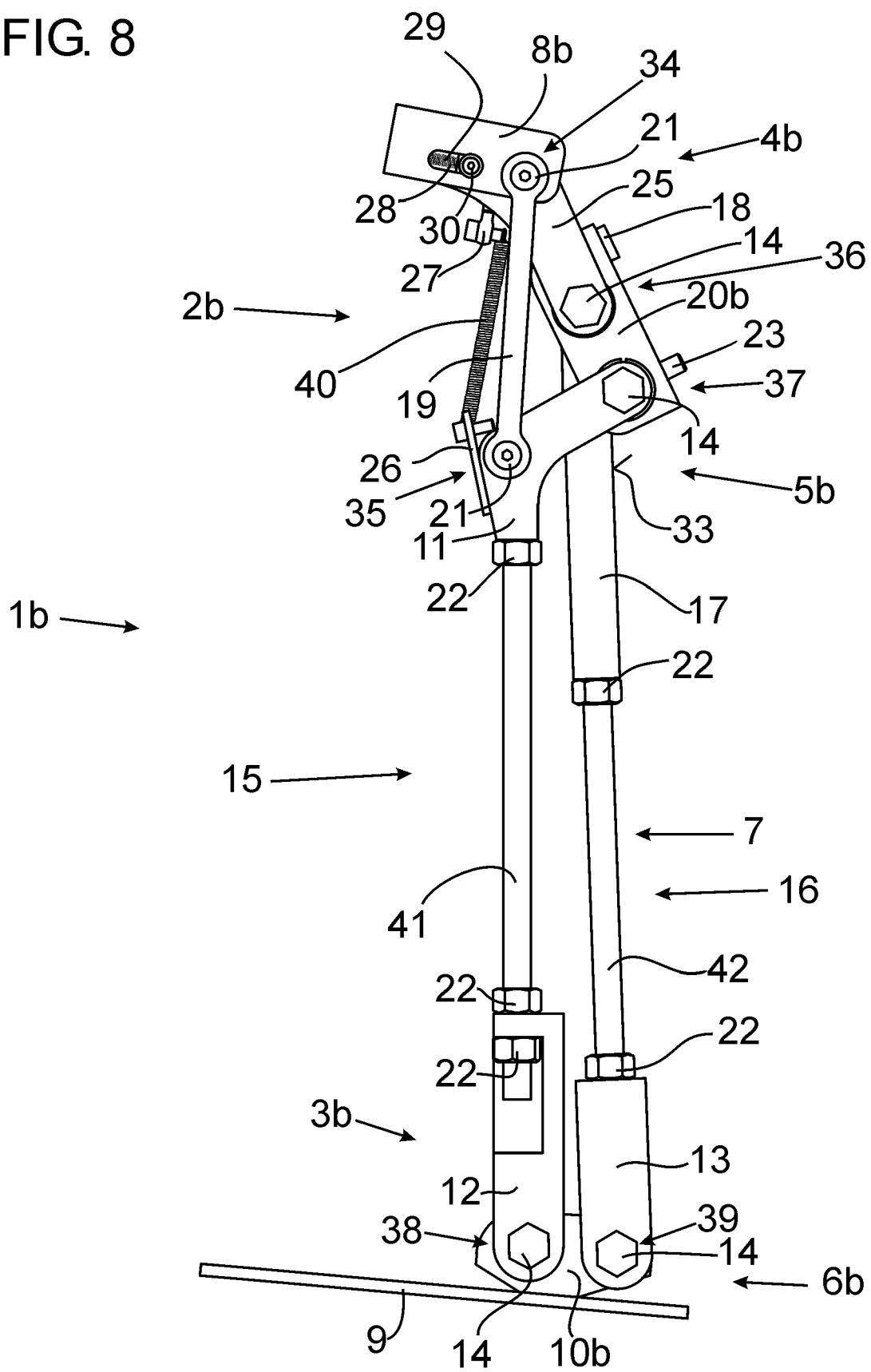
FIG. 8 shows a side view of the thigh prosthesis from FIG. 5 in a swing position of the knee joint.
Figure 9:
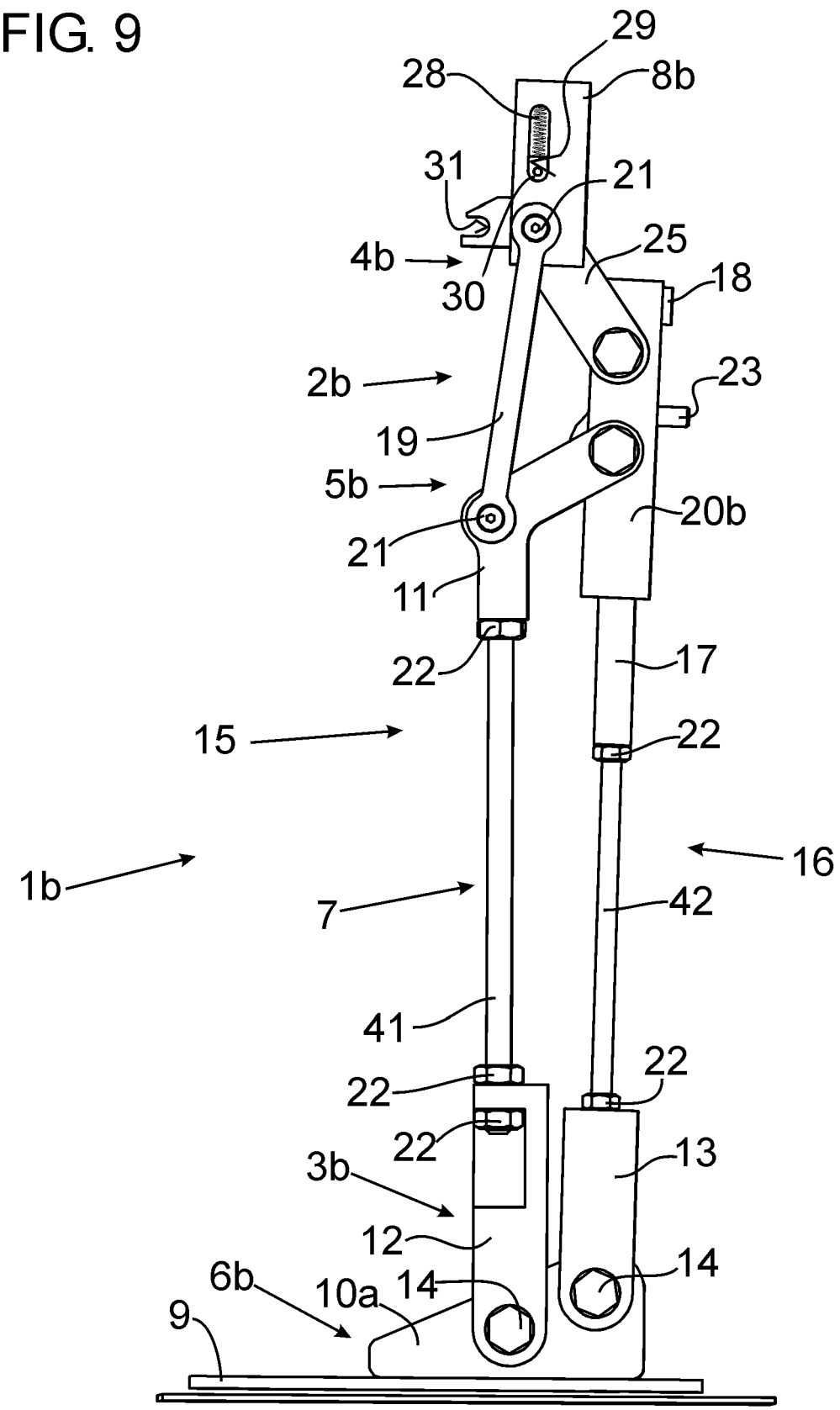
FIG. 9 shows a side view of the thigh prosthesis from FIG. 5 with a proximal knee joint upper part arranged in a seated position.
Figure 10:
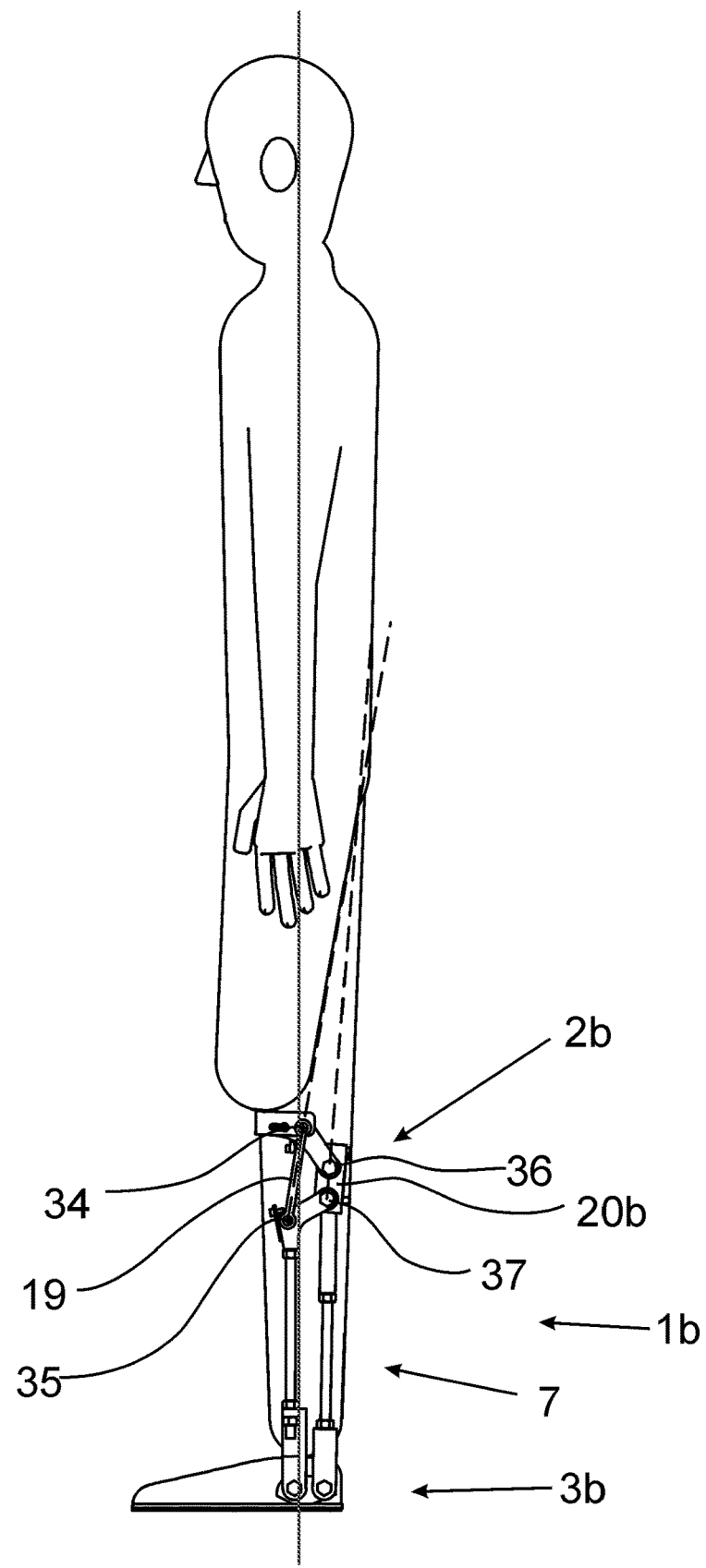
FIG. 10 shows the thigh prosthesis from FIG. 5 on a patient in a neutral position.

The thigh prosthetic component 1a can be adjusted between the stance position of the knee joint 2a shown in FIG. 1 to 3 and the swing position of the knee joint 2a shown in FIG. 4. When the thigh prosthetic component 1a is being used, i.e., in its position on a thigh stump of a patient, the knee joint 2a pivots out of the stance position into the swing position, i.e., a flexion of the knee joint 2a when the vector from of the body's center of gravity to the contact point on the ground by the thigh prosthetic component 1a is located behind the pivot point of the knee joint 2a. In this flexed position of the knee joint 2a, a flexion stop 18 arranged on the outside on the dorsal articulated arm 20a is in exterior contact with the shaft seat 8a and thereby restricts the maximum possible flexion angle of the knee joint 2a. In the flexed position of the knee joint 2a shown in FIG. 4 in which it is located in the swing position, there is a dorsal extension of the foot part 10a via the connection with the foot part 10a, which lifts the foot tip and thereby makes it possible for the thigh prosthetic component 1a to swing through easily.

Another exemplary embodiment of a thigh prosthetic component 1b is shown in FIG. 5 to 9 which largely corresponds to the thigh prosthetic component 1a shown in FIG. 1 to 4 in terms of basic construction and functioning. The ankle 3b of the foot part unit 6b differs from the ankle 3a of the thigh prosthetic component 1a only by an alternative embodiment of the foot part 10b of the foot part unit 6b. In the region of the knee joint 2b, the distal knee joint lower part 5b has a slight difference in comparison to the distal knee joint lower part 5a of the thigh prosthetic component 1a due to a shorter construction of the articulated arm 20b. Moreover, a spring seat 26 is arranged on the knee lower part 11.

A significant difference is however the construction of the proximal knee joint upper part 4b. In contrast to the proximal knee joint upper part 4a of the thigh prosthesis 1a, the shaft seat 8b is not designed as a single part but is instead articulated by the ventral upper knee joint axis 34 to a support 25 which, on its end opposite the shaft seat 8b, is also articulated by the dorsal upper knee joint axis 3b to the dorsal articulated arm 20b and the dorsal connecting element 16 composed of the coupling element 17 and dorsal lower leg rod 42. The articulated connection of the shaft seat 8b and dorsal support 25 makes it possible to pivot the shaft seat 8b relative to the support 25 between the walking position shown in FIG. 5 to 8 and the seated position shown in FIG. 9.

The shaft seat 8b can be locked by a locking body 30 in the walking position, wherein the locking body 30 is arranged in a latching recess 31 loaded by a spring element 28. To pivot the shaft seat 8b about the ventral upper knee joint axis 34, a shifting of the locking body 30 in a slot 29 out of the latching recess 31 counter to the spring force provided by the spring element 28 is necessary, wherein this displaces the locking body 30 in the slot 29. In the unlocked position, it is possible to pivot the shaft seat 8b out of the walking position shown in FIG. 5 to 8 into the seated position shown in FIG. 9 in which the shaft seat 8b is pivoted about the ventral upper knee joint axis 34. A spring element 40 furthermore extends between the spring seat 26 on the knee lower part 11 and a spring seat 27 on the support 25.

The functioning of the thigh prosthetic component 1b is shown in FIG. 10 to 16 in different positions of the gait phase of a patient. In the neutral position shown in FIG. 10, the vector from the body's center of gravity to the contact point on the ground runs in front of the pivot point of the knee joint 2b that results from the intersection of the lines (shown dashed in the figures) that extend on the one hand through the ventral upper and the ventral lower knee joint axis 34, 35 and on the other hand through the dorsal upper and dorsal lower knee joint axis 36, 37.

Figure 11:
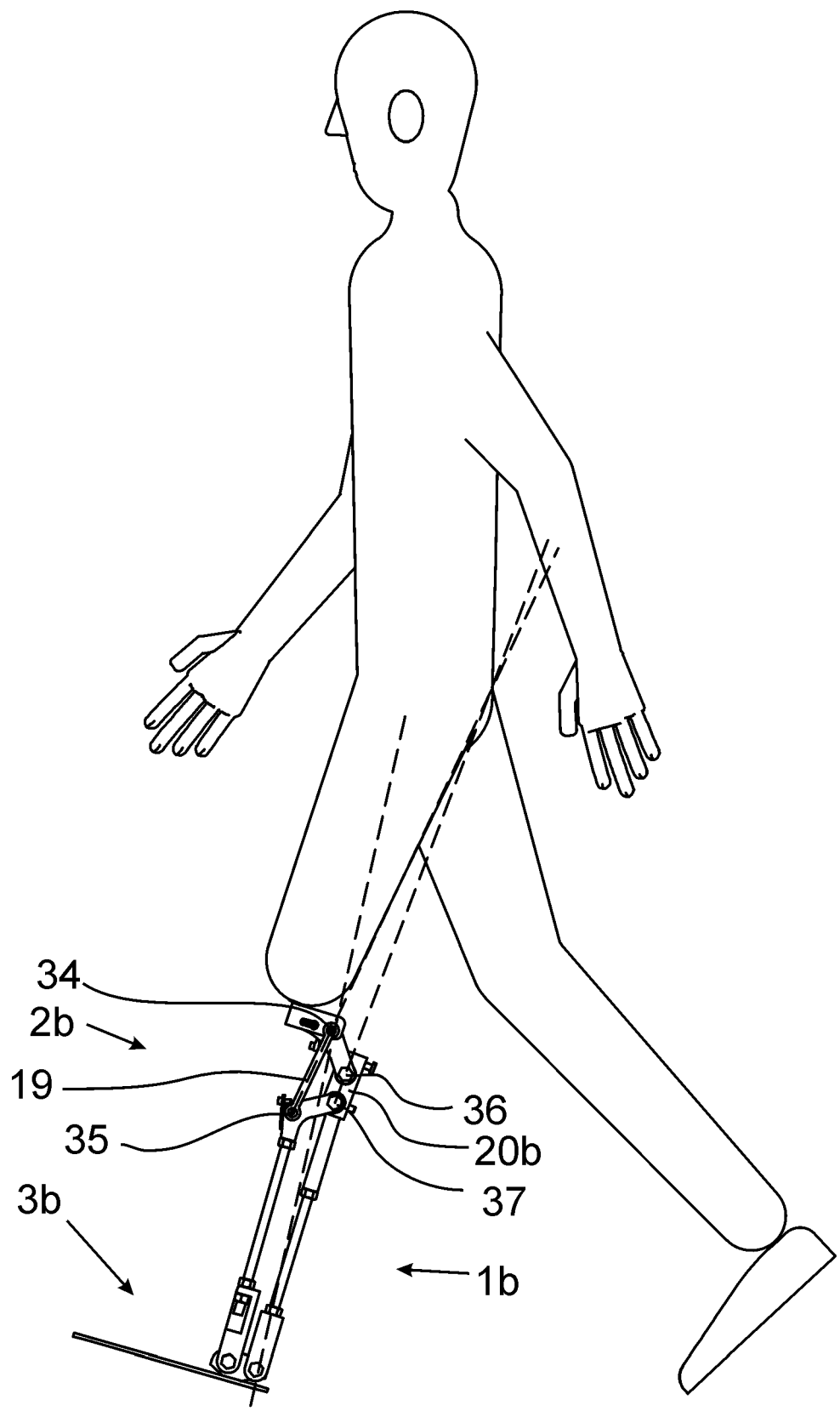
FIG. 11 shows the thigh prosthesis from FIG. 5 on a patient at the beginning of the stance phase of a gait phase.

FIG. 11 shows the position of a patient upon heel impact. The vector from the body's center of gravity to the contact point on the ground is clearly located in front of the pivot point and thereby ensures stable support by the thigh prosthetic component 1b.

Figure 12:
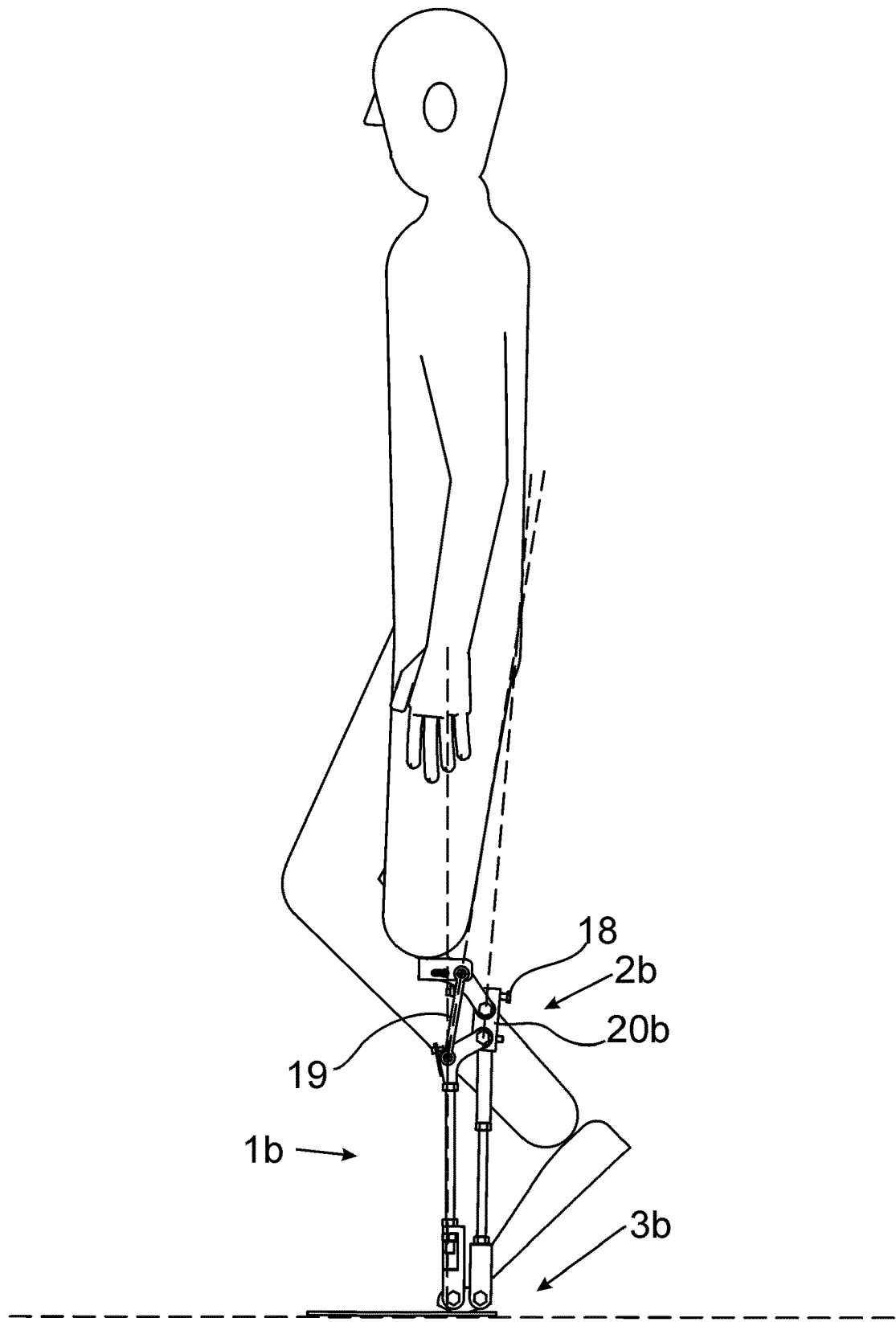
FIG. 12 shows the thigh prosthesis from FIG. 5 on a patient during the middle of the stance phase of a gait phase.

Also in the middle of the stance phase shown in FIG. 12, the resulting vector of the ground reaction forces clearly runs in front of the pivot point of the knee joint 2b and further ensures stable support by the thigh prosthetic component 1b.

Figure 13:
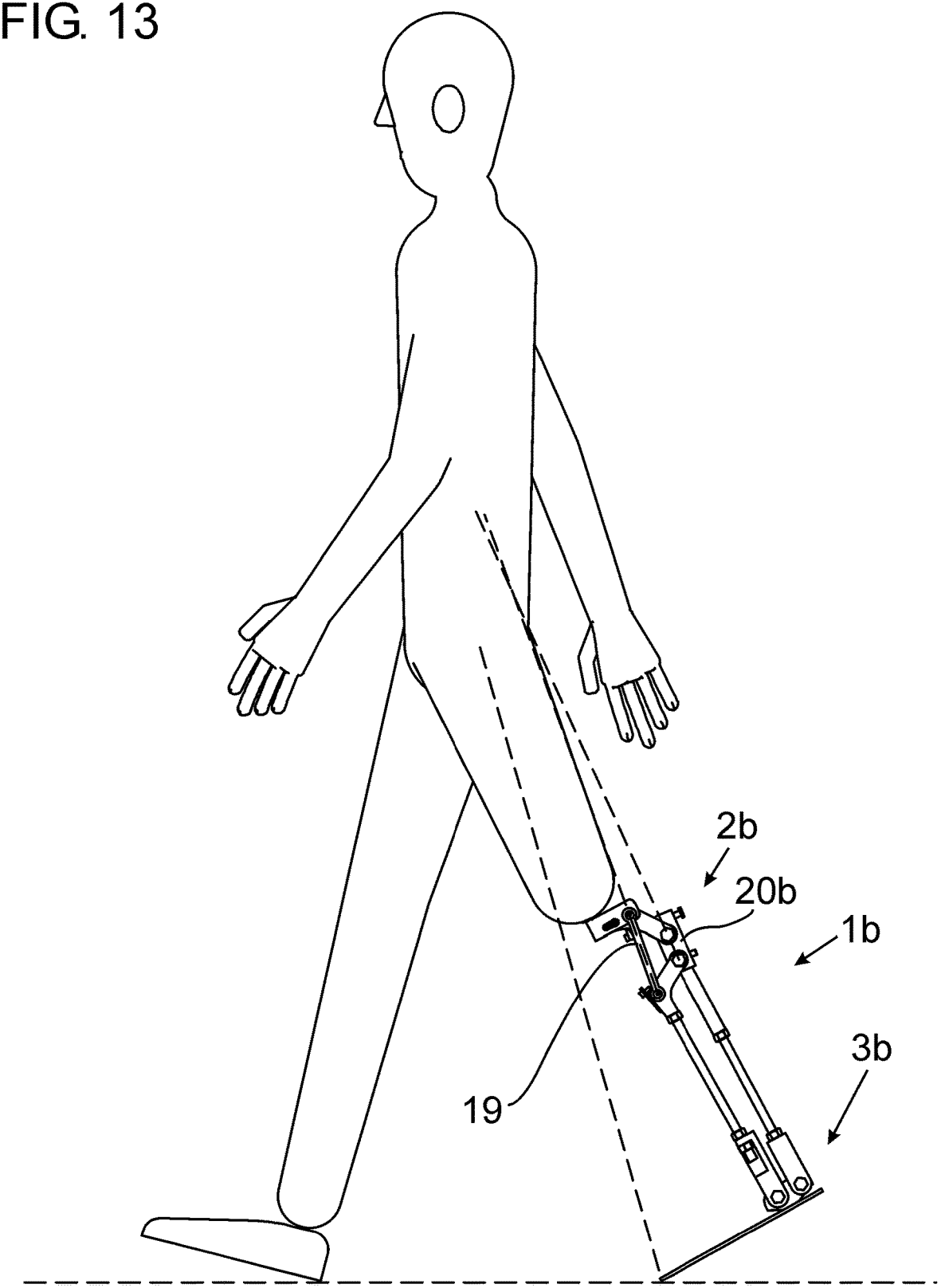
FIG. 13 shows the thigh prosthesis from FIG. 5 on a patient at the end of the stance phase of a gait phase.
Figure 14:
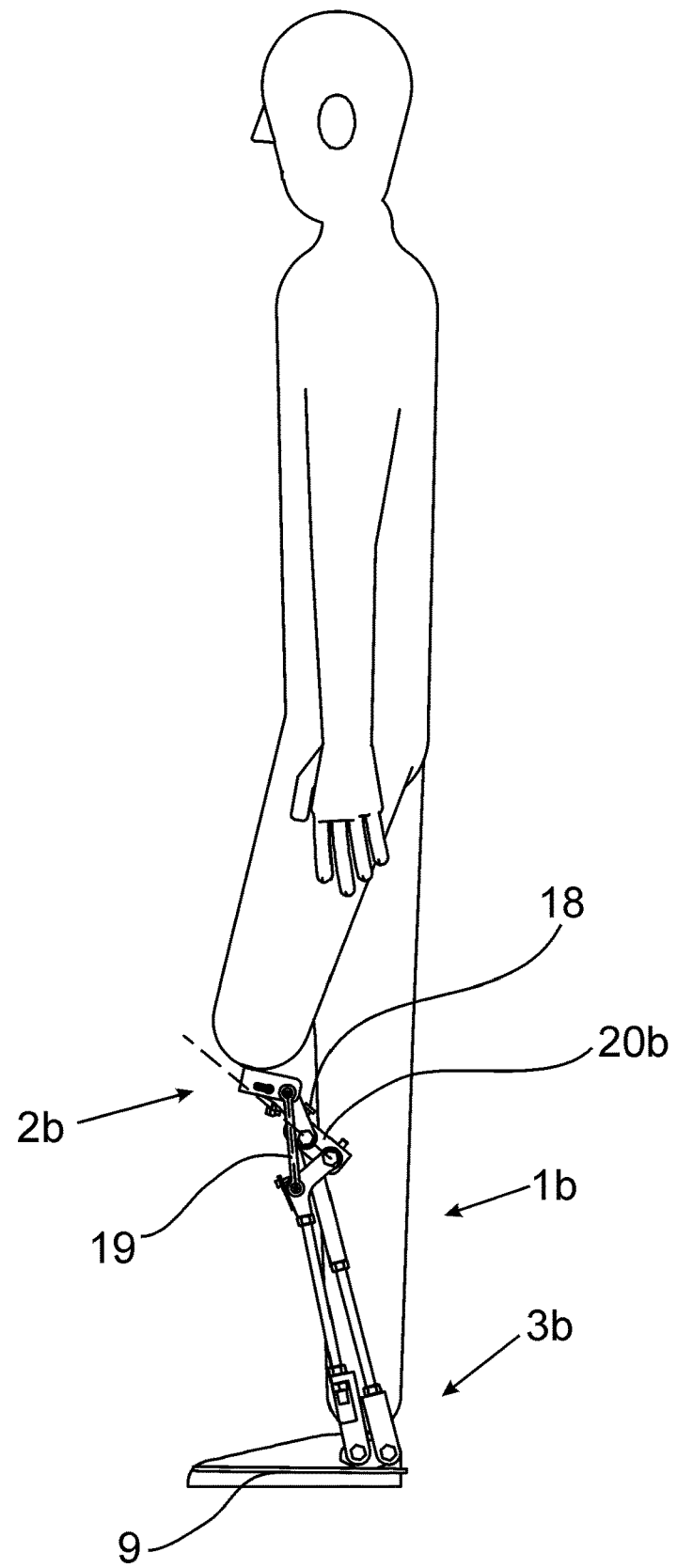
FIG. 14 shows the thigh prosthesis from FIG. 5 on a patient in the swing phase of a gait phase.

FIG. 13 shows the point in time shortly before toe-off. The momentary pivot point is still within a safe range in this position as well. However, the pivot point quickly approaches the resulting vector of the ground reaction forces under a forefoot load associated with slight hip flexing torque and then exceeds it, which results in a flexion of the knee joint 2b shown in FIG. 14 in which the thigh prosthetic component 1b is arranged in the swing phase, wherein a dorsal extension of the foot part 10b permits safe swing-through given the increased ground clearance.

At the end of the swing phase, heel contact again occurs as shown in FIG. 11, wherein the knee joint 2b is then again arranged in the stance position and ensures safe support for the user.

Figure 15:
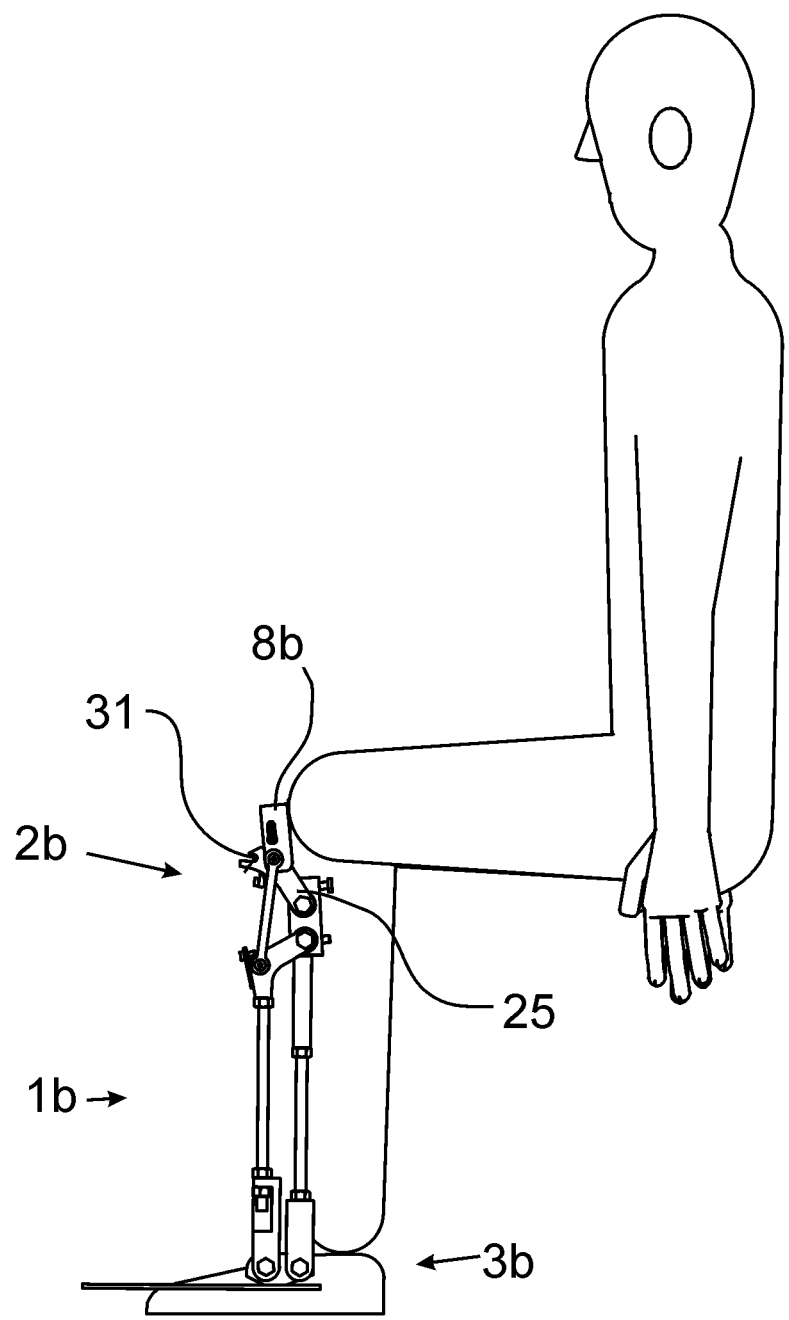
FIG. 15 shows the thigh prosthesis from FIG. 5 on a patient in a seated position.

In the position shown in FIG. 15, the shaft seat 8b is located in a pivoted seat position relative to the support 25. To reach this position, unlocking occurs in which the locking body 30 is manually moved out of the latching recess 31. After the seated position has ended, the shaft seat 8b enters its home position in which it independently enters the latching recess 31 due to the spring pretension of the locking body 30.

Figure 16:
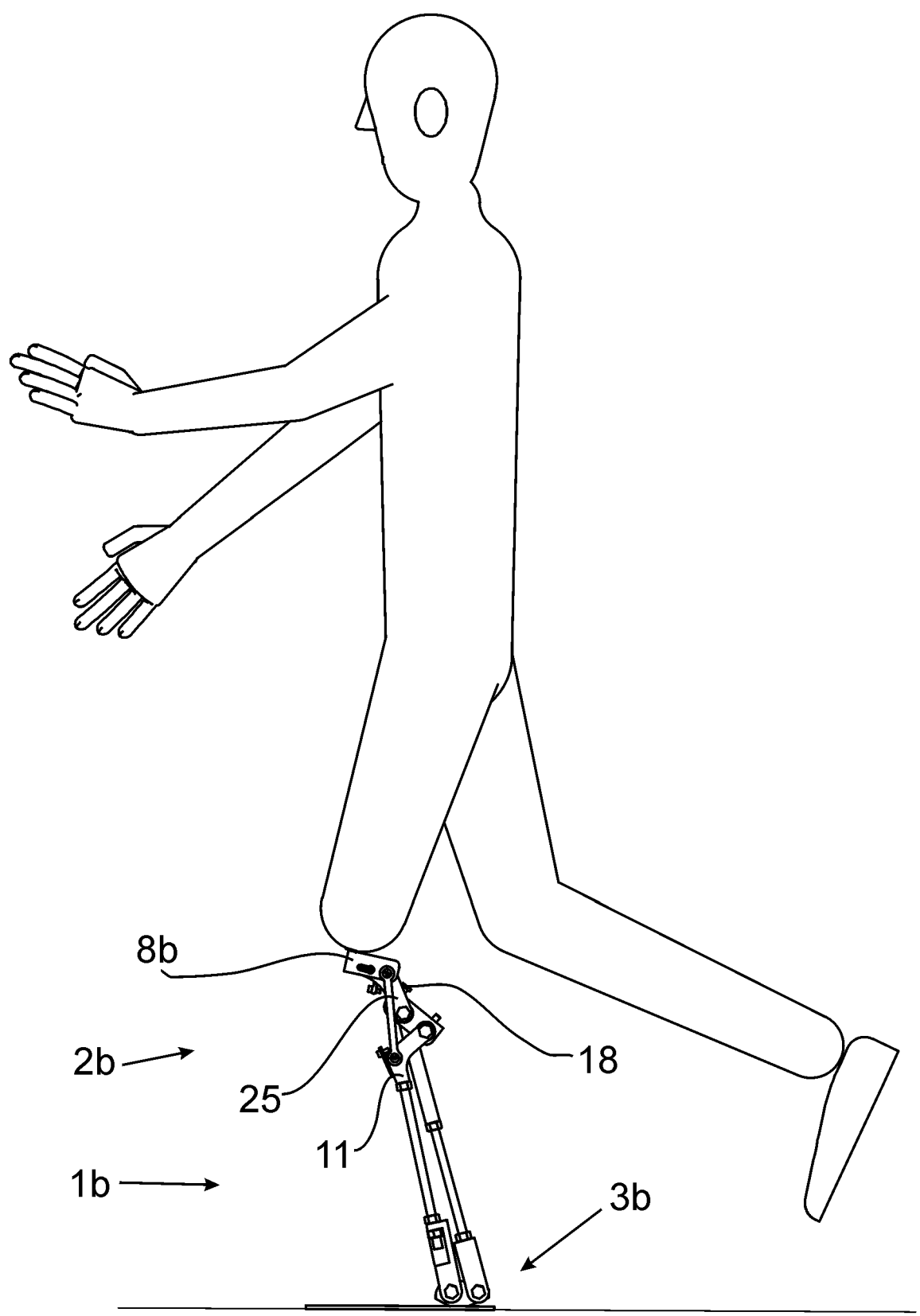
FIG. 16 shows the thigh prosthesis from FIG. 5 on a patient in a stumbling position.

FIG. 16 shows the situation of the thigh prosthetic component 1b while the patient is stumbling. Due to the flexion stop 18, knee flexion is restricted so that stable support in this position is ensured even while stumbling due to the limited flexion of the knee joint 2b from the flexion stop 18.

LIST OF REFERENCE SIGNS 1a, 1b Thigh prosthetic component
2a, 2b Knee joint
3a, 3b Ankle
4a, 4b Proximal knee joint upper part
5a, 5b Distal knee joint lower part
6a, 6b Foot part unit
7 Lower leg unit
8a, 8b Shaft seat
9 Foot plate
10a, 10b Foot part
11 Knee lower part
12 Ventral foot element
13 Dorsal foot element
14 Flathead screws
15 Ventral connecting element
16 Dorsal connecting element
17 Coupling element
18 Flexion stop
19 Ventral articulated arm
20a, 20b Dorsal articulated arm
21 Countersunk screw
22 Hexagon nut
23 Adjusting element/set screw
24 Shaft
25 Support
26 Spring seat
27 Spring seat
28 Spring element
29 Slot
30 Locking body
31 Latch recess
33 Stop surface
34 Ventral upper knee joint axis
35 Ventral lower knee joint axis
36 Dorsal upper knee joint axis
37 Dorsal lower knee joint axis
38 Ventral ankle axis
40 Spring element
41 Ventral lower leg rod
42 Dorsal lower leg rod

The invention claimed is:

1. A thigh prosthetic component for connecting to a thigh shaft, having:
a knee joint that can be pivoted between a stance position and a swing position and has a proximal knee joint upper part and a distal knee joint lower part which are connected by a ventral articulated arm and a dorsal articulated arm, wherein
the ventral articulated arm is articulated to the proximal knee joint upper part via a ventral, upper knee joint axis, and is articulated to the distal knee joint lower part via a ventral lower knee joint axis, and the dorsal articulated arm is articulated to the proximal knee joint upper part via a dorsal, upper knee joint axis, and is articulated to the distal knee joint lower part via a dorsal lower knee joint axis, and
an ankle for the pivotable connection of a foot part to a lower leg unit connected to the knee joint, wherein
the lower leg unit has a ventral connecting element and dorsal connecting element designed to transmit thrust and traction,
the ventral connecting element is pivoted at one end to the foot part by a ventral ankle axis and at the other end to the distal knee joint lower part, and the dorsal connecting element is articulated at one end to the foot part by a dorsal ankle axis and at the other end to the proximal knee joint upper part and the dorsal articulated arm by the dorsal upper knee joint axis such that an adjustment of the knee joint from the stance position into the swing position causes a dorsiflexion of the foot part,
an adjusting unit is configured to align the ventral articulated arm relative to the dorsal articulated arm in the stance position, and
the adjusting unit has an adjusting element that is adjustably mounted on the dorsal articulated arm and lies against a stop surface of the dorsal connecting element in the stance position.

2. The thigh prosthetic component according to claim 1, wherein the knee joint upper part and the knee joint lower part are operatively connected so that maximum flexion of the knee joint can be adjusted.

3. The thigh prosthetic component according to claim 1, wherein the dorsal articulated arm has a flexion stop lying against the proximal knee joint upper part in the swing position.

4. The thigh prosthetic component according to claim 3, wherein the flexion stop is adjustably arranged on the proximal knee joint upper part to establish the swing position.

5. The thigh prosthetic component according to claim 1, wherein the ventral connecting element or the dorsal connecting element are designed changeable in length.

6. The thigh prosthetic component according to claim 1, wherein the ventral connecting element has a ventral foot element articulated to the foot part and a ventral lower leg rod that is connected to the ventral foot element in a manner that can be adjusted in the direction of its longitudinal axis.

7. The thigh prosthetic component according to claim 1, wherein the dorsal connecting element has a dorsal foot element articulated to the foot part and a dorsal lower leg rod that is connected to the dorsal foot element in a manner that can be adjusted in the direction of its longitudinal axis.

8. The thigh prosthetic component according to claim 1, wherein the proximal knee joint upper part has a support and a shaft seat articulated to the support that can be adjusted between an upright position and seated position.

9. The thigh prosthetic component according to claim 8, wherein the support is articulated by the dorsal upper knee joint axis to the dorsal articulated arm and the dorsal connecting element, and is articulated by the ventral, upper knee joint axis to the shaft seat.

10. The thigh prosthetic component according to claim 8, wherein the shaft seat is unlockably locked on the support in the upright position, whereby accidentally adjusting the proximal knee joint upper part from the upright to the seated position is effectively prevented by a locking body that can be adjusted between a locked position and an unlocked position which is arranged on the shaft seat and can be brought into engagement with a latching recess in the support in the locked position.

11. The thigh prosthetic component according to claim 8, wherein the shaft seat is pretensioned on the support in the direction of the upright position such that the pretension is blocked in the seated position to prevent the thigh prothesis from independently assuming the upright position in a seated state due to unblocked pretension.

12. The thigh prosthetic component according to claim 8, wherein a locking body that can be adjusted between a locked position and an unlocked position is arranged on the shaft seat and can be brought into engagement with a latching recess in the support in the locked position.

13. The thigh prosthetic component according to claim 12, wherein the locking body is pretensioned in the direction of the locked position.

14. The thigh prosthetic component according to claim 1, wherein the ventral connecting element has a ventral foot element articulated to the foot part and a ventral lower leg rod that is connected to the distal knee joint lower part in a manner that can be adjusted in the direction of its longitudinal axis.

15. The thigh prosthetic component according to claim 1, wherein the dorsal connecting element has a dorsal foot element articulated to the foot part and a dorsal lower leg rod that is connected to the proximal knee joint upper part in a manner that can be adjusted in the direction of its longitudinal axis.

16. A thigh prosthetic component for connecting to a thigh shaft, having:
- a knee joint that can be pivoted between a stance position and a swing position, and has a proximal knee joint upper part and a distal knee joint lower part which are connected by a ventral articulated arm and a dorsal articulated arm, wherein
- the ventral articulated arm is articulated to the proximal knee joint upper part via a ventral, upper knee joint axis, and is articulated to the distal knee joint lower part via a ventral lower knee joint axis, and the dorsal articulated arm is articulated to the proximal knee joint upper part via a dorsal, upper knee joint axis, and is articulated to the distal knee joint lower part via a dorsal lower knee joint axis, and
- an ankle for the pivotable connection of a foot part to a lower leg unit connected to the knee joint, wherein—
- the lower leg unit has a ventral connecting element and dorsal connecting element designed to transmit thrust and traction, wherein
- the ventral connecting element is pivoted at one end to the foot part by a ventral ankle axis and at the other end to the distal knee joint lower part, and the dorsal connecting element is articulated at one end to the foot part by a dorsal ankle axis and at the other end to the proximal knee joint upper part and the dorsal articulated arm by the dorsal upper knee joint axis such that an adjustment of the knee joint from the stance position into the swing position causes a dorsiflexion of the foot part whereby in the swing position there is a dorsiflexion of the foot part via the connection with the knee, which lifts the foot tip.

* * * * *